United States Patent [19]

Scoggin

[11] 4,347,385
[45] Aug. 31, 1982

[54] PROCESS FOR THE SEPARATION OF SULFUR COMPOUNDS FROM WATER

[75] Inventor: Jack S. Scoggin, Bartlesville, Okla.

[73] Assignee: Phillips Petroleum Company, Bartlesville, Okla.

[21] Appl. No.: 254,230

[22] Filed: Apr. 14, 1981

[51] Int. Cl.³ .................. C02F 1/04; C07C 149/06
[52] U.S. Cl. ........................ 568/72; 203/11; 203/76; 203/77; 203/98; 203/DIG. 14
[58] Field of Search ............... 203/10, 11, 12, 14, 203/98, DIG. 14, 91, 74, 76, 77, 85; 568/72, 73; 423/563; 208/208 R

[56] References Cited

U.S. PATENT DOCUMENTS

| | | | |
|---|---|---|---|
| 2,427,309 | 9/1947 | Schulze | 568/72 |
| 3,054,727 | 9/1962 | Von Kessel et al. | 203/77 |
| 3,083,231 | 3/1963 | Ray | 568/73 |
| 3,333,019 | 7/1967 | Nathan et al. | 203/12 |
| 3,335,071 | 8/1967 | Bollen et al. | 203/85 |
| 3,404,072 | 10/1968 | Bollen et al. | 203/11 |
| 3,551,102 | 12/1970 | Hettick et al. | 23/193 |
| 3,847,570 | 11/1974 | Gunther | 55/73 |
| 4,138,309 | 2/1979 | Kühnlein et al. | 203/12 |
| 4,260,462 | 4/1981 | Didycz et al. | 203/11 |

Primary Examiner—Wilbur L. Bascomb, Jr.

[57] ABSTRACT

Sulfur compounds are separated from aqueous mixtures containing same by employing a stripper having at least two stripping sections with at least a portion of the stripper kettle product being recycled to the lower stripping section. The process is particularly effective in recovering mercaptans from steam condensate. In the production of mercaptans by reacting hydrogen sulfide with olefins, steam condensate contaminated with mercaptans is obtained from the steam ejector employed in the product fractionation column.

4 Claims, 2 Drawing Figures

PROCESS FOR THE SEPARATION OF SULFUR COMPOUNDS FROM WATER

This invention relates to a process for the removal of sulfur compounds, e.g., mercaptans, from water. In another aspect, this invention relates to the removal of mercaptans from water using a stripper having at least two stripper sections with recycle of at least a portion of the bottoms taken from the stripper to the lower section. In another aspect, this invention relates to a process for removing mercaptans from steam condensate obtained from the product fractionation column in a process for producing mercaptans. In still another aspect, this invention relates to a process for treating steam condensate obtained from a process for producing normal dodecylmercaptan and tertiary dodecylmercaptan.

BACKGROUND OF THE INVENTION

In the production of mercaptans by reacting hydrogen sulfide with olefins, e.g., producing normal dodecylmercaptan and tertiary dodecylmercaptan (n-$C_{12}$SH and t-$C_{12}$SH) by reacting $H_2S$ with the $C_{12}$ olefins, a waste steam condensate stream is obtained when steam jets are used in separating the sulfur product. The steam jets are used to pull a vacuum on the product distillation columns, e.g., normal and tertiary dodecylmercaptan distillation columns. The steam condensate stream from the steam ejector is contaminated with mercaptans and other substances from a fractionation column. Problems with the disposal of the sulfur contaminated steam condensate and with effective separation of the sulfur compounds from the steam condensate have been encountered. It would be most desirable to separate the mercaptan from water and then reuse the two components.

In order to recover both mercaptan and water separately, the steam condensate can be fed to a single section stripper to strip the mercaptan from water. However, the efficiency and economy of such a system can be improved.

An object of the present invention, therefore, is to provide a more efficient and effective process for separating sulfur and its compounds from water.

Another object of this invention is to provide a process employing a stripper wherein the process provides a flexibility in the loading of liquid to the stripper to thereby maintain an optimum operating condition in the stripper.

Still another object of this invention is to provide a process which solves the problem of disposing of sulfur contaminated water, especially steam condensate obtained from a product fractionation column in a process for producing mercaptans.

Other objects, aspects, and the several advantages of this invention will become apparent to those skilled in the art upon a study of this disclosure, the appended claims, and the drawings.

SUMMARY OF THE INVENTION

In accordance with the invention, sulfur-containing compounds, e.g., mercaptans, present in aqueous streams are separated therefrom by stripping in a multiple stripping section stripping zone under conditions which substantially remove the sulfur-containing compound(s) overhead and an aqueous stream substantially freed of sulfur compounds as bottoms.

In a specific embodiment, a steam condensate containing sulfur-containing compounds, e.g., mercaptans, is passed to a stripping zone having at least two stripping sections wherein the condensate is subjected to conditions which remove the sulfur compounds overhead and leaves a bottoms aqueous stream substantially free of sulfur compounds. The overhead stream containing the sulfur-containing compounds and water is cooled to form a condensate which is separated into an organic phase comprising the sulfur-containing compounds and an aqueous phase which is partly or wholly recycled to the stripping zone. In addition, at least a portion of the bottoms stream is recycled to the lower most stripping section of the stripping zone.

In an actual operation of a preferred embodiment of the invention, sulfur and its compounds are separated from water by feeding the aqueous stream to a stripper column having at least two stripping sections. Overhead is removed from the stripper with the sulfur compounds being recovered by phase separation. Bottoms is removed and at least a portion is recycled to the lower most stripping section thereby maintaining an optimum operating condition in the stripper as well as increasing the stripping efficiency of the stripper.

The process of this invention is particularly useful in separating mercaptans from water. The process is especially useful as a last step in a process for making mercaptans wherein steam ejectors are used to pull a desired vacuum condition in the mercaptan distillation volumn. The process of this invention can be employed to remove mercaptans in an efficient manner from the mercaptan contaminated steam condensate obtained from the steam ejectors.

DETAILED DESCRIPTION OF THE INVENTION

A process for separating sulfur and its compounds from water would be very useful and find many applications, e.g., recovering mercaptan and water from steam condensate obtained from the steam ejector in a products fractionation column. One possible method is to use a simple distillation column for separating the sulfur compound from the water. For example, in a process for producing mercaptans which employs a steam ejector with the product distillation column mercaptan contaminated steam condensate is frequently obtained. In order to recover both the mercaptan and water separately, steam condensate can be fed to a single section stripper to strip mercaptan from water. Overhead vapor can be condensed and phase separated. The water phase can be partly or wholly recycled to the stripper feed. The mercaptan phase can be recycled to an upstream stripper to remove hydrogen sulfide, or to an upstream olefin purification column to remove olefins from mercaptans. The stripper kettle product can be sent to further processing, such as treatment employed in a sewage plant or further chemical treatment for cooling tower water make-up. Although the use of a simple stripper for separating a sulfur compound from water is straightforward, the method is not always as efficient and effective as can be hoped for.

Figure 1:
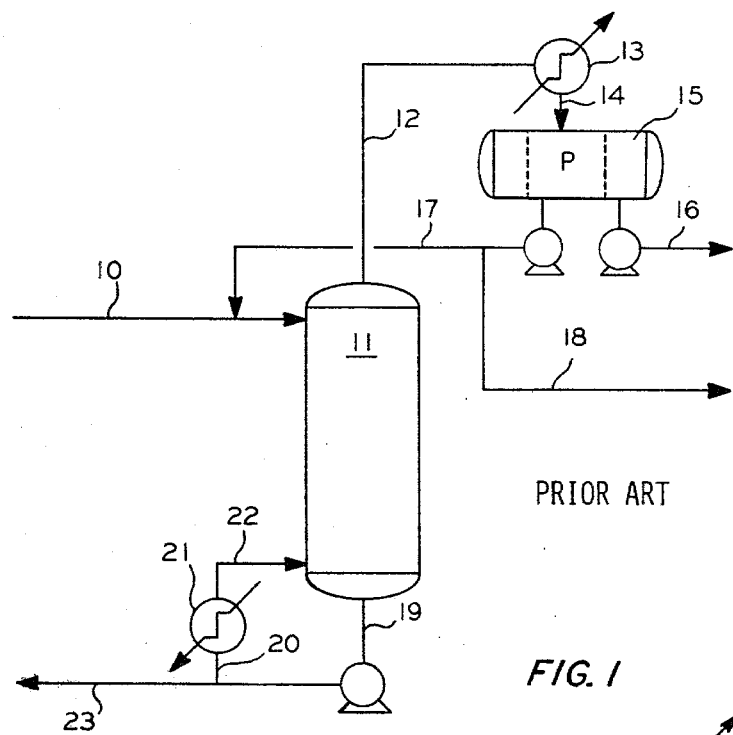
FIG. 1 depicts a single stripping section stripper.

Referring now to FIG. 1, FIG. 1 depicts a process using a single section stripper. The mercaptan of sulfur compound contaminated aqueous stream is passed via 10 into the top of stripper 11. Overhead is taken via 12, passed through heat exchange means 13, and to phase separator 15 via conduit means 14. In phase separating means 15, an aqueous phase is taken with a portion 17 being recycled to feed stream 10 and another portion 18 being passed onto further use. A sulfur compound or mercaptan phase 16 is also passed on for further use or further processing.

Kettle product or stripper bottoms are taken at 19 with a portion 20 being heated with heat exchange means 21 and recycled via 22 as stripping steam to the kettle. Another portion of the bottom is passed to further processing via 23.

The following is an example of material flow and typical operating conditions that will be employed in a single stripping section stripper as shown in FIG. 1.

| Stream No. |
|---|
| 10. Feed, mercaptan and water, 1500 lb/hr. 200° F., 65 psia |
|     Mercaptan = 1.2 lb/hr. |
|     Water = 1498.8 lb/hr. |
| 11. Single - stripping section stripper |
|     212–281° F. |
|     14.7–50 psia |
| 12. Overhead product, mercaptan and H$_2$O, |
|     750 lb/hr. H$_2$O, 180° F., 16 psia |
|     Mercaptans = 1.7775 lb/hr. |
| 13. Cooler 755,000 Btu/hr. |
| 14. Overhead product leaving cooler 180° F. |
| 15. Separator |
| 16. Liquid mercaptan 1.775 lb/hr., 180° F., 16 psia |
| 17. Water for reflux 500 lb/hr., 180° F., 65 psia |
| 18. Recovered water for disposal, |
|     250 lb/hr, 227° F., 19.8 psia |
| 19. Bottom product, mercaptan and H$_2$O, |
|     1998.8 lb/hr., 227° F., 19.8 psia |
|     Mercaptan = 0.036 lb/hr. |
| 20. Portion of bottom product for reboiler vapor |
|     750 lb/hr., 227° F., 19.8 psia |
| 21. Heater 778,000 Btu/hr. |
| 22. Stripping stream 227° F. |
| 23. Portion of bottom product for further processing, |
|     12488 lb/hr., 227° F., 19.8 psia |
|     Mercaptan = 0.0225 lb/hr. |

The following data illustrates a batch distillation procedure and a continuous distillation procedure for the fractionation of samples of n-C$_{12}$SH condensate and t-C$_{12}$SH condensate obtained from a steam ejector in a process for producing the mercaptans by reacting H$_2$S with olefins. The distillation employed a single stripping section stripper.

TABLE I

Steam jet condensates from the manufacture of normal dodecylmercaptan and tertiary dodecylmercaptan (n-C$_{12}$SH and t-C$_{12}$SH) were distilled (separately) in a packed column at atmospheric pressure with the purpose of reducing the mercaptan contents in the kettle products.

| Feed Analyses: | Organic C, mg/l | H$_2$S mg/l | C$_{12}$=, mg/l | —SH, mg/l | Total S, mg/l |
|---|---|---|---|---|---|
| n-C$_{12}$SH Condensate | 120 | 0 | <2 | 11 | 80 |
| t-C$_{12}$SH Condensate | 310 | 440 | 8 | 2000 | 3500 |

Batch Distillation Data:

Run Conditions Boilup Return to Column, Analyses of Kettle Product Supernate

| | Organic | H$_2$S | C$_{12}$=, | —SH, | Total S, |

TABLE I-continued

Steam jet condensates from the manufacture of normal dodecylmercaptan and tertiary dodecylmercaptan (n-C$_{12}$SH and t-C$_{12}$SH) were distilled (separately) in a packed column at atmospheric pressure with the purpose of reducing the mercaptan contents in the kettle products.

| Feed | % | C, mg/l | mg/l | mg/l | mg/l | mg/l |
|---|---|---|---|---|---|---|
| n-C$_{12}$SH Condensate | 95 | 110 | 0 | <2 | 9 | 60 |
| t-C$_{12}$SH Condensate | 95 | 13 | 0 | <2 | 6 | 20 |

TABLE II

Normal dodecylmercaptan (n-C$_{12}$SH) steam jet condensate and tertiary dodecylmercaptan (t-C$_{12}$SH) steam jet condensate were distilled separately on a 20-tray Oldershaw column. The continuous feed was at the top of the column. A trap below the condenser allowed the condensation rate to be measured and a manual overhead product to be removed manually. The kettle product was removed continuously.

| Feed Analyses: | COD, mg/l | H$_2$S, mg/l | C$_{12}$=, mg/l | —SH, mg/l | Total S, mg/l |
|---|---|---|---|---|---|
| n-C$_{12}$SH Condensate | 4.2 | 0 | <2 | 2 | 120 |
| t-C$_{12}$SH Condensate | 397 | 64 | <2 | 132 | 180 |

Continuous Distillation Data:

| | Run Conditions | | | Analyses | |
|---|---|---|---|---|---|
| Feed | Overhead Product, Vol % of Feed | Column Feed Rate ml/min | Volume Ratio, Boilup to Feed | Water Phase Overhead Condensate COD, mg/l | Kettle Prod. Supernate COD, mg/l |
| n-C$_{12}$SH Cond | 0 | 20 | 0.2:1 | 168 | 0.3 |
| n-C$_{12}$SH Cond | 0 | 15 | 0.4:1 | — | 0.8 |
| n-C$_{12}$SH Cond | 0 | 8.5 | 0.5:1 | 252 | 1.6 |
| t-C$_{12}$SH Cond | 5 | 20 | 0.25:1 | 1900 | 10 |
| t-C$_{12}$SH Cond | 5 | 15 | 0.33:1 | 1200 | 13 |

NOTES:
(1) The Fractionation efficiency varied more with column loading than with the boilup to feed ratio.
(2) In the n-C$_{12}$SH condensate distillation with no overhead product take off, no separate organic phase, the organic content of the overhead condensate was a function of run time.
(3) In the t-C$_{12}$SH condensate distillation with an organic phase condensing, organic content of the water phase should be close to saturation.

The batch distillation showed little removal of organics from the n-C$_{12}$SH condensate feed in the kettle product, but the continuous distillation did. The t-C$_{12}$SH condensate feed produced a column overhead product that condensed into organic and water phases. The small overhead organic phase remained in the trap while reflux from the water phase returned to the column. The continuous t-C$_{12}$SH condensate kettle products had a mild onion odor and the continuous n-C$_{12}$SH condensate kettle products had almost no odor. The continuous overhead water phase products had a strong mercaptan odor.

These experimental results show that a single-section stripper removes most of the mercaptans from n-dodecylmercaptan condensate, but not as efficiently for t-dodecylmercaptan condesate. It is the object of this invention to improve separation of sulfur compounds in general, and in particular, of mercaptans, from water by using a stripper having at least two stripping sections with recycle of at least a part of the stripping kettle product to the lower stripping section of the stripper. Use of the two-stripping-section stripper increases the stripping efficiency of the stripper allows the stripper to maintain an optimum operating condition.

Figure 2:
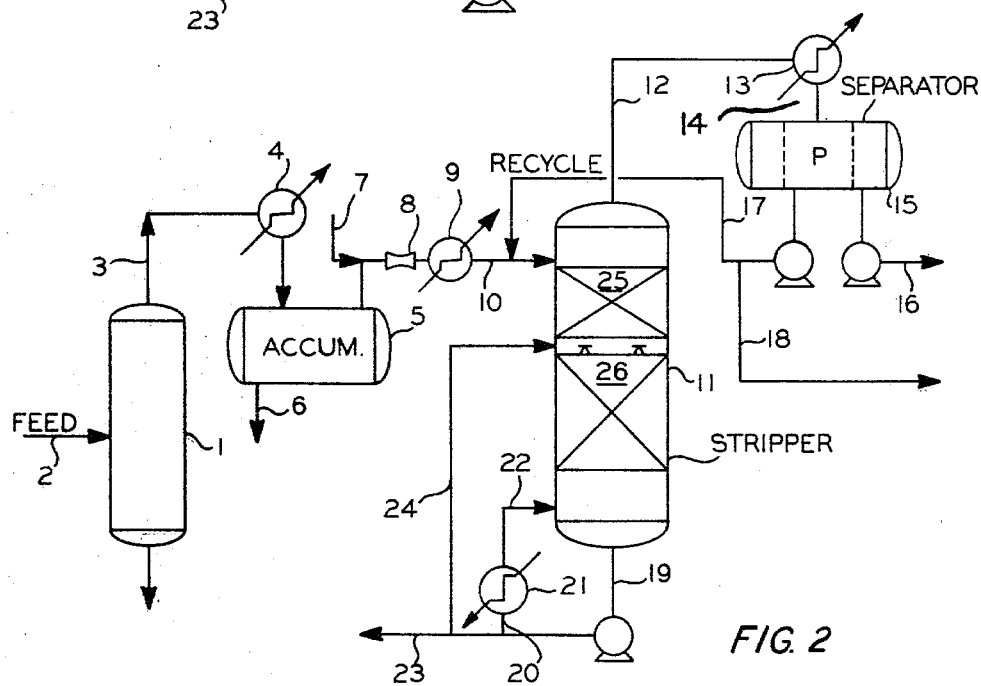
FIG. 2 depicts a two stripping section stripper as employed in the process of the present invention.

Referring now to FIG. 2, a feedstream comprising mercaptans, H₂S (trace) and olefins is passed by line 2 and introduced into vacuum fractionation zone 1 wherein the feed is subjected to conditions such that the mercaptans are taken overhead by line 3 and olefins are removed as bottoms from column 1. The overhead streams comprising mercaptans is cooled in condenser 4 and the condensate formed is passed to accumulator 5. Liquid mercaptan is withdrawn from accumulator 5 by line 6. Gases present in accumulator 5 are removed through multiple stage ejector 8 due to the introduction of steam by line 7. Steam and gases withdrawn from accumulator 5 are passed through cooler 9 and cooled sufficiently to form a condensate in line 10.

The following is an example of material flow and typical operating conditions that can be employed in the operation of vacuum fractionation column 1 and steam ejector 8 described above.

Steam No.

1. Fractionation column, 387° F., 1 Torr (1 mm mercury)
2. Feed, 2167 lb. mercaptans, trace H₂S and C₁₂ olefins, 225° F., 6 Torr
3. Overhead vapor, 2166 lb mercaptans
4. And 9, condensers, 1,152,000 Btu/hr.
5. Accumulator, 100° F.
6. Liquid mercaptan, 2166 lb/hr.
7. Steam to steam ejector, 1499 lb/hr., 200 psia
8. Steam ejector, 4 stages
10. Condensate to two-stripping section, 1500 lb/hr., 200° F., 65 psia
    Mercaptan = 0.08 wt. %
    Water = 99.92 wt. %

A sulfur compound containing aqueous stream is passed via 10 into the top of upper stripping section 25 of stripper 11. As in the single section stripper, overhead 12 is passed to a phase separating means 15 via heat exchanger means 13 and conduit means 14. Mercaptan or sulfur compound phase is removed via 16 and passed for further use. Aqueous phase is recovered with a portion optionally being recycled via 17 to feedstream 10 and the remainder being passed via 18 for further treatment or use.

Bottoms, primarily water, is recovered at 19 with a portion 20 being recycled to the kettle via heater means 21 and conduit means 22 in order to supply stripping steam for the stripper. Another portion is passed to further use or treatment via 23 with a third portion being passed via conduit means 24 to the top of lower stripping section 26. The recycle of a part of the kettle product to the lower stripping section increases stripping efficiency and also loads liquid to the stripper in a manner such that an optimum operating condition is maintained. The recycle of the kettle bottoms to the top of the column 11 would only dilute the overhead product thereby requiring additional heat energy for the separation.

The two stripping sections are different with respect to the type of packing or plate structure therein with the type of material one wishes to separate and the degree of separation one wishes to achieve dictating the type of packing, plate, or tray structure in the two stripping sections. For example, in the separation of mercaptans from water, the upper section would have a packing or tray structure suitable for a more highly concentrated mercaptan aqueous stream whereas the lower section would be packed in order to accommodate the separation of less concentrated mercaptan aqueous stream. One skilled in the art could easily determine the most appropriate type of packing for a particular sulfur compound-water separation.

Applicable packings which may be used in the two stripping sections include ceramic, chemical porcelain, carbon steel and stainless. Raschig rings and lessing rings made of carbon, chemical porcelain and polypropylene; Berl Saddles, made of chemical stoneware and chemical porcelain; Intalox Saddles, made of polypropylene; Tellerette, made of polyethylene and Pall ring, made of polyethylene. Pall ring and Intallox saddle packings are preferred.

The operating conditions of the two stripping section stripper can vary, and again, are dependent upon the materials being separated and the degree of separation that one wishes to achieve.

Shown below are ranges of operating conditions for the various applicable streams in the two-stripper operation.

Stream No.

10. Feed, 1000–3000 lb/hr., 150–210° F., 50–100 psia
    Mercaptans = 0.05–0.2 wt. %
11. Two-stripping-section stripper
    upper section 220–240° F., 18–22 psia
    lower section 220–250° F., 18–23 psia
12. Overhead product, 500–1500 lb/hr., 150–200° F., 15–20 psia
13. Cooler 1,500,000–2,500,000 Btu/hr.
14. Overhead product leaving cooler, 150–200° F.
16. Liquid mercaptan, 0.5–6 lb/hr., 150–200° F., 15–20 psia
17. Water for reflux, 300–1000 lb/hr., 150–200° F., 15–20 psia
18. Recovered water for reuse, 150–500 lb/hr., 220–240° F., 18–22 psia
19. Bottom product, 3600–12000 lb/hr., 220–240° F., 18–22 psia
    Mercaptans = 0.0005–0.0015 wt. %
20. Portion of bottom product for reboiler vapor, 1000–4000 lb/hr., 220–240° F. 18–22 psia
21. Heater, 1,000,000–4,000,000 Btu/hr.
22. Stripping stream, 220–240° F.
23. Portion of bottom product for further processing, 800–2500 lb/hr., 220–240° F., 18–22 psia
24. Portion of bottom product for recycle to the lower stripping zone, 1800–5500 lb/hr., 220–240° F., 18–22 psia The following calculated example illustrates material flow and typical operating conditions that can be used in a two stripping section stripper as shown in FIG. 2. The operating conditions disclosed, however, are merely illustrative and are not meant to be limiting in any manner to the invention.

Stream No.

10. Feed, mercaptan and H₂O, 1500 lb/hr., 200° F., 65 psia
    Mercaptans = 0.08 wt. %
11. Two-stripping-section stripper
    upper section 227° F., 19.7 psia
    lower section 228° F., 20.1 psia
12. Overhead product, 750 lb/hr., 180° F., 16 psia -continued

| Stream No. | |
|---|---|
| 13. | Cooler 2,013,000 Btu/hr. |
| 14. | Overhead product leaving cooler 180° F. |
| 15. | Separator |
| 16. | Liquid mercaptan,<br>1.08 lb/hr., 180° F., 16 psia |
| 17. | Water for reflux,<br>500 lb/hr., 180° F., 65 psia |
| 18. | Recovered water for reuse,<br>250 lb/hr., 228° F., 20.1 psia |
| 19. | Bottom product,<br>5998.8 lb/hr., 228° F., 20.1 psia<br>Mercaptan = 0.00096 wt. % |
| 20. | Portion of bottom product for reboiler vapor<br>2000 lb/hr., 228° F., 20.1 psia |
| 21. | Heater<br>2,036,200 Btu/hr |
| 22. | Stripping stream 228° F. |
| 23. | Portion of bottom product for further processing,<br>1248.8 lb/hr. 228° F., 20.1 psia<br>Mercaptans = 0.12 lb/hr. |
| 24. | Portion of bottom product for recycle to the lower stripping zone 2750 lb/hr., 20.1 psia |

The calculated example of the two stripping section stripper shows that about 200% more mercaptan is removed from the kettle product than in the single stripping section stripper. The duel section stripper with recycle of a portion of the bottoms product to the lower stripping section, therefore, provides a more efficient and effective way of removing sulfur compounds, e.g., mercaptans, from water.

Although the present invention has been described in conjunction with specific embodiments thereof, it is evident that many alternatives, modifications, variations and equivalents will be apparent to those skilled in the art in light of the foregoing disclosure of the invention. Accordingly, it is expressly intended that all such alternatives, modifications, variations and equivalents which fall within the spirit and scope of the invention as defined in the dependent claims be embraced thereby

I claim:

1. In a process for the production of mercaptans by reacting hydrogen sulfide and olefins with the reaction product being separated in a fractionation column employing a steam ejector and forming a steam condensate stream from the steam ejector effluent which is contaminated with mercaptans and other materials from the fractionation column and said mercaptans being separated from the steam condensate stream from the steam ejector by distillation wherein the improvement comprises separating the mercaptans from said steam condensate stream by feeding said condensate to a stripper having at least two stripping sections operated under conditions to remove a vaporous stripper overhead stream and a stripper bottoms aqueous stream, and recycling a portion of said stripper bottoms stream to an upper portion of the lowermost stripping section of said stripper.

2. The process of claim 1 wherein said mercaptans are selected from the group consisting of normal dodecylmercaptan, tertiary dodecylmercaptan, and mixtures thereof.

3. The process of claim 1 wherein said stripper overhead is condensed and phase separated into an aqueous phase and a mercaptan-containing phase with at least a portion of said aqueous phase being recycled to the feed to the stripper, and another portion of said stripper bottoms is recycled to the reboiler section of said stripper for use as stripping vapor.

4. The process of claim 3 wherein said mercaptans are selected from the group consisting of normal dodecylmercaptan, tertiary dodecylmercaptan, and mixtures thereof.

* * * * *